United States Patent [19]

Buechler

[11] Patent Number: 5,331,109
[45] Date of Patent: Jul. 19, 1994

[54] PHENCYCLIDINE DERIVATIVES AND PROTEIN AND POLYPEPTIDE PHENCYCLIDINE DERIVATIVE CONJUGATES AND LABELS

[75] Inventor: Kenneth F. Buechler, San Diego, Calif.

[73] Assignee: Biosite Diagnostics Incorporated, San Diego, Calif.

[21] Appl. No.: 864,104

[22] Filed: Apr. 6, 1992

[51] Int. Cl.⁵ .................. C07K 17/02; A61K 39/385; C07C 333/08; C07D 211/00
[52] U.S. Cl. .................... 530/404; 530/405; 530/406; 530/408; 435/188; 435/964; 436/543; 436/544; 546/213
[58] Field of Search ............... 546/213; 530/404–406, 530/408–410; 435/964, 188; 436/543, 544, 501

[56] References Cited

U.S. PATENT DOCUMENTS

| | | | |
|---|---|---|---|
| 4,231,999 | 11/1980 | Carlsson et al. | 435/7.9 |
| 4,232,119 | 11/1980 | Carlsson et al. | 435/7.9 |
| 4,281,065 | 7/1981 | Lin et al. | 435/188 |
| 4,446,065 | 5/1984 | Lin et al. | 530/389.8 |
| 4,695,624 | 9/1987 | Marburg et al. | 530/404 |
| 5,155,212 | 10/1992 | Dubler et al. | 530/380 |

FOREIGN PATENT DOCUMENTS 0284413  9/1988  European Pat. Off. .

OTHER PUBLICATIONS

Reid et al (1990) Neuropharmacology 29(11):1047-53.
Blair et al (1983) J. Immunol. Methods 59:129-143.
Jung et al (1981) Biochem. Biophys. Res. Commun. 101(2):599-606.
Rowley et al (1975) J. Biol. Chem. 250(10):3759-3766.

*Primary Examiner*—Kay K. Kim
*Attorney, Agent, or Firm*—Lyon & Lyon

[57] ABSTRACT

The present invention is directed to novel PCP derivatives which are synthesized for the covalent attachment to antigens or receptors (proteins or polypeptides) for the preparation of antibodies or receptors to PCP and PCP analogue metabolites. The resulting novel antigens may be used for the production of antibodies or receptors using standard methods. Once generated, the antibodies and the novel derivatives which are covalently attached to proteins, polypeptides or labels may be used in the immunoassay process.

4 Claims, 1 Drawing Sheet

EXAMPLE 4

EXAMPLE 5

EXAMPLE 4

EXAMPLE 5

PHENCYCLIDINE DERIVATIVES AND PROTEIN AND POLYPEPTIDE PHENCYCLIDINE DERIVATIVE CONJUGATES AND LABELS

FIELD OF THE INVENTION

This invention is in the field of ligand receptor assays, including immunoassays, for the detection of selected metabolites of phencyclidine in a fluid sample. More particularly, this invention relates to methods for the synthesis of novel phencyclidine derivatives and protein and polypeptide phencyclidine derivative conjugates and labels for use in the preparation of antibodies to phencyclidine metabolites and for use in the immunoassay process.

BACKGROUND OF THE INVENTION

Phencyclidine (PCP) was developed as an anesthetic for humans but has become a highly abused drug. The illicit use of PCP and PCP analogues, such as cyclohexamine, phenylcyclohexylpyrrolidine, phenylcyclopentylpiperidine and thienylcyclohexylpiperidine has resulted in a medical need for antibodies and diagnostics to rapidly detect the PCP and PCP analogue metabolites in order to monitor and treat PCP abuse.

The preparation of antibodies to PCP and PCP analogues requires the synthesis of a PCP derivative in order to covalently attach the derivative to an antigenic polypeptide or protein. In addition, the PCP derivative is covalently attached to various polypeptides, proteins or labels for use in screening antibodies and in the immunoassay process. The PCP derivative should mimic the structure of the PCP and PCP analogue metabolites sought to be measured. Therefore, the selection and synthesis of the types of PCP derivatives for covalent attachment to proteins, polypeptides or labels is critical. In addition, the PCP derivatives need to be stable to hydrolysis in an aqueous solution.

PCP compounds and conjugates for immunization and immunoassay have been described in U.S. Pat. Nos. 4,281,065 and 4,446,065.

SUMMARY OF THE INVENTION

The present invention is directed to novel PCP derivatives which are synthesized for the covalent attachment to antigens (proteins or polypeptides) for the preparation of antibodies to PCP and PCP analogue metabolites. The resulting novel antigens may be used for the production of antibodies using standard methods. Once generated, the antibodies and the novel derivatives which are covalently attached to proteins, polypeptides or labels may be used in the immunoassay process.

DEFINITIONS

In accordance with the present invention and as used herein, the following terms, are defined with the following meanings, unless explicitly stated otherwise.

"Drug" shall mean any compound or ligand which either as a result of spontaneous chemical reaction or by enzyme catalyzed or metabolic reaction, generates an intrinsic activity when administered to a biological system. The drug may be metabolized to a derivative of the drug by a biological system. Common examples of drugs and their metabolites are morphine, barbiturates, tetrahydrocannbinol, phencyclidine, amphetamines, methamphetamines, opiates, benzodiazepines, cocaine, estrone-3-glucuronide, pregnanediol-glucuronide, cotinine, lysergic acid diethylamide, propoxyphene, methadone, anabolic steroids and tricyclic anti-depressants.

"Drug derivative" shall mean a ligand derivative, drug, drug metabolite or a drug analogue conjugated to a linking group.

"Drug metabolite" shall mean a compound upstream or downstream from a drug in a biochemical or metabolic pathway, or an intermediate.

"Label" shall mean a signal development element or a means capable of generating a signal, for example, a dye or an enzyme. The attachment of a drug derivative to the label can be through covalent bonds, adsorption processes, hydrophobic and/or electrostatic bonds, as in chelates and the like, or combinations of these bonds and interactions.

"Binding domain" shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

"Linking group" shall mean the composition between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1–20 carbons and 0–10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon-carbon bonds are acceptable examples of chemically compatible linking groups. Other chemically compatible compounds which may comprise the linking group are set forth in this Definition section and hereby are incorporated by reference.

"Hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

"Aryl" shall refer to aromatic groups which have at least one ring having a conjugated pi electron system and includes carbocyclic aryl, heterocyclic aryl and biaryl groups, all of which may be optionally substituted.

"Carbocyclic aryl groups" shall refer to groups wherein the ring atoms on the aromatic ring are carbon atoms. Carbocyclic aryl groups include monocyclic carbocyclic aryl groups and optionally substituted naphthyl groups.

"Monocyclic carbocyclic aryl" shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

"Optionally substituted naphthyl" shall refer to 1- or 2-naphthyl or 1- or 2-naphthyl preferably substituted by lower alkyl, lower alkoxy or halogen.

"Heterocyclic aryl groups" shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

"Optionally substituted furanyl" shall refer to 2- or 3-furanyl or 2- or 3-furanyl preferably substituted by lower alkyl or halogen.

"Optionally substituted pyridyl" shall refer to 2-, 3- or 4-pyridyl or 2-, 3- or 4-pyridyl preferably substituted by lower alkyl or halogen.

"Optionally substituted thienyl" shall refer to 2- or 3-thienyl, or 2- or 3-thienyl preferably substituted by lower alkyl or halogen.

"Biaryl" shall refer to phenyl substituted by carbocyclic aryl or heterocyclic aryl as defined herein, ortho, meta or para to the point of attachment of the phenyl ring, advantageously para; biaryl is also represented as the —C$_6$H$_4$—Ar substituent where Ar is aryl.

"Aralkyl" shall refer to an alkyl group substituted with an aryl group. Suitable aralkyl groups include benzyl, picolyl, and the like, and may be optionally substituted.

"Lower" referred to herein in connection with organic radicals or compounds respectively defines such with up to and including 7, preferably up to and including 4 and advantageously one or two carbon atoms. Such groups may be straight chain or branched.

The terms (a) "alkyl amino" (b) "arylamino" and (c) "aralkylamino" respectively shall refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl—CO—or HCO—.

The terms "acylamino" refers to RCONCR)—and (RCO$_2$N—respectively, wherein each R is independently hydrogen or hydrocarbyl.

The term "hydrocarbyloxycarbonyloxy" shall refer to the group ROC(O)O—wherein R is hydrocarbyl.

The term "lower carboalkoxymethyl" or "lower hydrocarbyloxycarbonylmethyl" refers to hydrocarbyl—OC(O)CH$_2$—with the hydrocarbyl group containing ten or fewer carbon atoms.

The term "carbonyl" refers to —C(O)—.

The term "carboxamide" or "carboxamido" refers to —CONR$_2$ wherein each R is independently hydrogen or hydrocarbyl.

The term "lower hydrocarbyl" refers to any hydrocarbyl group of ten or fewer carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "hydrocarbyloxycarbonylamino" refers to a urethane, hydrocarbyl—O—CONR—wherein R is H or hydrocarbyl and wherein each hydrocarbyl is independently selected.

The term "di(hydrocarbyloxycarbonyl)amino" refers to (hydrocarbyl—O—CO)$_2$N—wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methine" refers to

The term "methylene" refers to —CH$_2$—.

The term "alkylene" refers to a divalent straight chain or branched chain saturated aliphatic radical.

The term "oxy" refers to —O—(oxygen).

The term "thio" refers to —S—(sulfur).

"Disulfide" refers to —S—S—.

"Thioester" refers to —S—O—.

"Thioether" refers to C—S—C.

"Ester" refers to

"Analyte" shall mean substance of natural or synthetic origin sought to be detected and/or measured, said substance having a specific binding partner capable of a specific interaction with said analyte.

"Ligand" shall mean a binding partner to a ligand receptor. A substance which, if detected may be used to infer the presence of an analyte in a sample, including, without limitation, haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefor, i.e., the ligand receptor of a ligand-receptor assay.

"Receptor" shall mean a receptor capable of binding ligand, typically an antibody, or a fragment thereof, but which may be another ligand, depending on assay design.

"Ligand-Receptor Assay" shall mean an assay for an analyte which may be detected by the formation of a complex between a ligand and a ligand receptor which is capable of a specific interaction with that ligand. Ligand-Receptor assays may be competitive or non-competitive, homogeneous or heterogeneous.

"Immunogen" shall mean a chemical or biochemical structure, determinant, antigen or portion thereof, which elicits an immune response, including, for example, polylysine, bovine serum albumin and keyhole limpid hemocyanin (KLH).

"Antigenic" shall mean a chemical or biochemical structure, determinant, antigen or portion thereof which is capable of inducing the formation of an antibody.

DETAILED DESCRIPTION OF THE PREFERRED EMBODIMENTS

Figure 1:
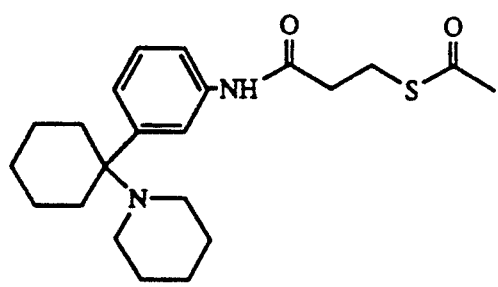
FIG. 1 depicts the structures of the compounds synthesized in Examples 4, and 5, which are metaAcetylthiopropionamide Phencyclidine, and meta-3-Mercaptopropionamide Phencyclidine, respectively.
Figure 1:
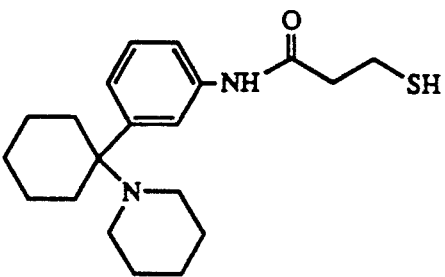

Novel compounds are described which are used in the generation of antibodies and in the immunoassay process generally. The compounds are derivatives of PCP and PCP metabolites. The derivatization of the PCP analogue for covalent attachment to proteins, polypeptides and labels occurs on the phenyl ring so that the character of the PCP analogue can be presented to the antibody or receptor in a manner which allows for the desired binding interaction. The synthesis of the linking group between the protein, polypeptide or label and the PCP derivative is designed to achieve the desired binding of the drug derivative and the receptor. For example, the derivative may be displaced from the surface of the protein, polypeptide or label to allow the derivative to present itself to the binding domain of receptors.

In general, the compounds of this invention have the following formula:

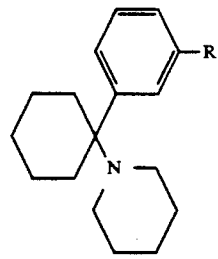

where R is a linking group comprising one of the following:

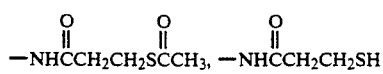

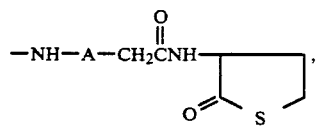

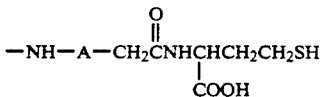

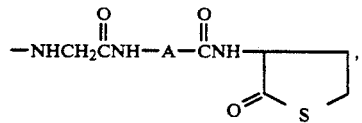

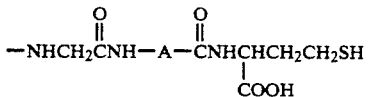

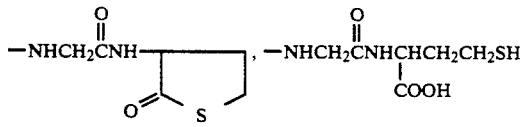

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label derivatized via an amide, disulfide, thioether, or ester bond to the molecule or label to a compound of the formula is of the following:

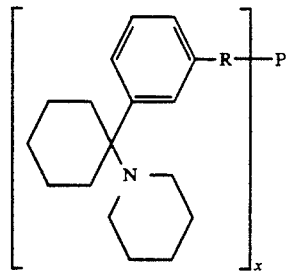

where P is an antigenic protein or polypeptide or a protein, polypeptide or label;
where x is at least one and not greater than 100;
where R is a linking group of the following:

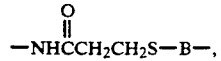

-continued

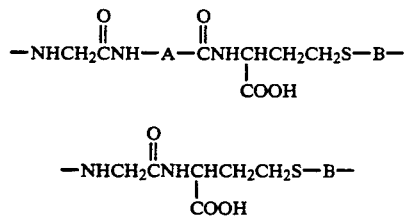

where A is a linking group of from 1 to 20 carbons and 0 to 10 heteroatoms (NH, O, S) either branched or straight chain;

where B is a linking group ultimately attached to a protein, polypeptide or label selected from the group comprising:

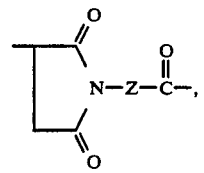

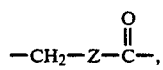

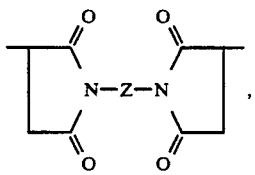

—S—,

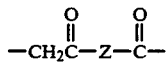

where Z is a linking group of from 1 to 20 carbons and 0 to 10 heteroatoms (NH, O, S) and may be branched or straight chain.

The preferred (best mode) compounds of this invention have the following formula:

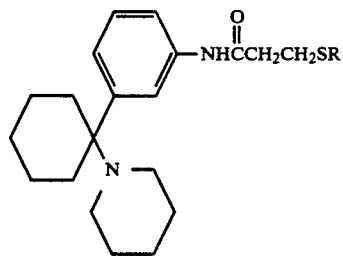

where R is —H

In addition, the general form of the preferred (best mode) immunogenic protein or polypeptide molecule or the protein or polypeptide molecule or label derivatized via an amide or ester bond to the molecule or label to a compound of the formula is of the following:

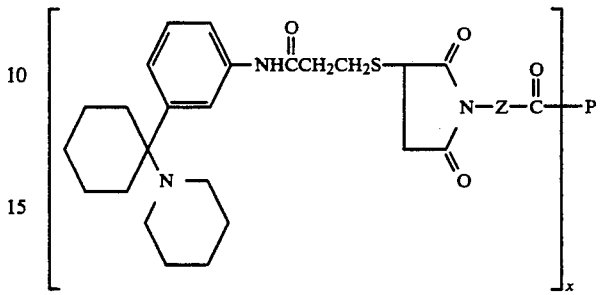

where P is an antigenic protein or polypeptide or a protein, polypeptide or label;

where x is at least one and not greater than 100;

where Z is a linking group of from 1 to 20 carbons and 0 to 10 heteroatoms (NH, O, S) and may be branched or straight chain.

Of particular interest are PCP derivatives which have been nitrated at the meta position of the phenyl ring and subsequently reduced to the amino PCP derivative. This amino PCP can be utilized for elaboration of the linking group which attaches the derivative to the protein, polypeptide or label. The elaboration of the linking group from the aromatic amine or off an aromatic hydroxyl of a PCP analogue can be performed using various chain length alkyl halide carboxylic acids, for example, 3-iodopropionic acid to form an N-alkylated or O-alkylated carboxylic acid PCP derivative, respectively, which can then be further reacted with an amino alkyl thiolester, such as homocysteine thiolactone, to synthesize the thiol ester derivative of the PCP. In a preferred mode, the linking group can be elaborated from the aromatic amine or hydroxyl using various chain lengths of carboxylic acid alkyl thiol esters, for example, 3-acetylthiol propionic acid. The thiol esters of the resulting derivative are hydrolyzed in dilute base, for example, 0.01M-0.1M potassium hydroxide, to generate the thiol group which is reacted with the thiol reactive group, such as a maleimide, an alkyl halide or a thiol. Those skilled in the art can recognize the versatility of synthetic strategies described herein.

The compounds are synthesized as thiols or thiol esters so that their covalent attachment to proteins, polypeptides or labels can easily be performed under mild conditions, for example, pH 7 in a protein solution. The protein, polypeptide or label is reacted with a reagent which incorporates a maleimide or alkylhalide into the molecule. These reagents and methods for their use are available from Pierce, Rockford, IL, for example, for incorporation of maleimide groups onto proteins, polypeptides or labels one can use succinimidyl 4-(N-maleimidomethyl)cyclohexane-1-carboxylate (SMCC), succinimidyl 4-(p-maleimidophenyl)butyrate (SMPB) or m-maleimidobenzoyl-N-hydroxysuccinimide ester (MBS). For introduction of an alkyl halide into a protein, polypeptide or label one can use N-succinimidyl(4-iodoacetyl)aminobenzoate (SIAB) also from Pierce. The thiol reactive group, such as maleimide, an alkyl halide or a thiol can be incorporated into the protein, polypeptide or label prior to reaction with the drug thiol, but the drug thiol can also be reacted with the thiol reactive compound prior to reaction with the protein, polypeptide or label. Also, bis-maleimide compounds of varying length can be reacted with thiol containing proteins, polypeptides or labels for covalent coupling of the PCP thiol derivatives. Conversely, the bis-maleimide compound can be reacted with the thiol derivative and subsequently to the thiol containing protein, polypeptide or label. Common bis-maleimides are bis-maleimidohexane from Pierce, N,N'-bis(3-maleimidopropionyl)-2-hydroxy-1,3-propanediamine from Sigma Chemical Co., St. Louis, Mo., and 1,1'-(methylenedi-4,1-phenylene)bismaleimide from Aldrich Chem. Co., Milwaukee, Wis. The thiol PCP derivatives can also form disulfides with thiol containing polypeptide, protein or label molecules as a means to incorporate the derivative into the molecule.

The use of drug derivatives, immunogens and protein and polypeptide conjugates for generating antibodies and for use in the immunoassay process is described, for example, in U.S. Pat. Nos. 4,067,774, 4,446,065, 5,028,535 and 5,089,391.

Experimental Examples

Example 1

Synthesis of meta-Nitrophencyclidine

To an ice cooled solution of phencyclidine hydrochloride (5 g, $1.8 \times 10^{-2}$ mol) in concentrated sulfuric acid (9 ml) was added dropwise, and with stirring, fuming nitric acid (2 ml). The reaction mixture was stirred in an ice-water bath for 1 hour and then poured onto crushed ice/water. The mixture was made basic with 10N sodium hydroxide (50 ml) to pH 12 and extracted with diethyl ether (2×100 ml). The combined organic layers were washed with water (2×100 ml), dried over anhydrous magnesium sulfate, filtered and evaporated under vacuum. The residue was treated with methyl alcohol (20 ml) and heated on a hot water bath (80° C.) until solute dissolved. The flask was covered with aluminum foil (product is light sensitive) and the solution was allowed to stir at room temperature overnight when a yellow solid precipitated. The solid was collected by filtration and dried under vacuum to afford 3.0 g (58%) of m-nitrophencyclidine as fine yellow crystals which were protected from light: mp 81°-82° C.

Example 2

Synthesis of meta-Aminophencyclidine

To a stirring solution of m-nitrophencyclidine (3.0 g, $10.4 \times 10^{-3}$ mol) in methyl alcohol (150 ml) was added, under a flow of argon, 10% palladium-carbon (0.5 g) followed by ammonium formate (4.0 g, $6.3 \times 10^{-2}$ mol). The reaction mixture was stirred at room temperature for 2 hours after which time the catalyst was removed by filtration and the solvent was evaporated under vacuum. The residue was treated with 1N potassium hydroxide solution (30 ml) and extracted with diethyl ether (2×50 ml). The combined organic extracts were washed with water (50 ml), dried over anhydrous magnesium sulfate, filtered and evaporated under vacuum. The residue was dissolved in hexane (20 ml) and the solution was stirred at room temperature overnight when a white solid precipitated. The solid was collected by filtration and dried under vacuum to afford 1.4 g (52%) of m-aminophencyclidine: mp 121°-122° C.

Example 3

Synthesis of Acetylthiopropionic Acid

To a stirred solution of 3-mercaptopropionic acid (7 ml, 0.08 moles) and imidazole (5.4 g, 0.08 moles) in tetrahydrofuran (THF, 700 ml) was added dropwise over 15 minutes, under argon, a solution of 1-acetyl imidazole (9.6 g, 0.087 moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5-2. The mixture was extracted with diethyl ether (2×50 ml), the ether was washed with water (2×50 ml) and dried over magnesium·sulfate and evaporated. The residual crude yellow oily solid product (10.5 g) was recrystallized from chloroform-hexane to afford 4.8 g (41% yield) acetylthiopropionic acid as a white solid with a melting point of 44°-45° C.

Example 4

Synthesis of meta-Acetylthiopropionamide Phencyclidine

To a stirring solution of m-aminophencyclidine (1.4 g, $5.4 \times 10^{-3}$ mol) and acetylthiopropionic acid (0.87 g, $5.8 \times 10^{-3}$ mol) in anhydrous tetrahydrofuran (7 ml) was added dicyclohexylcarbodiimide (1.19 g, $5.8 \times 10^{-3}$ mol). The flask was purged with argon and the solution stirred at room temperature for 2 hours. The mixture was filtered from insoluble dicyclohexylurea and evaporated under vacuum. The residual solid was recrystallized from chloroform/hexane to afford 1.5 g (71%) of m-acetylthiopropionamide phencyclidine as a white crystalline solid: mp 152°-4° C.

Example 5

Synthesis of meta-3-Mercaptopropionamide Phencyclidine meta-Acetylthiopropionamide phencyclidine (0.01 g, $2.57 \times 10^{-5}$ mol) was dissolved in 1.29 ml 0.12M potassium carbonate in 80% methanol/20% water (v/v). The solution sat at room temperature for 5 minutes and then 0.2 ml 0.5M potassium phosphate, pH 7, was immediately added and the solution was adjusted to pH 7-7.5 with hydrochloric acid (1N). The title compound in solution was used as is to react with thiol reactive groups, such as maleimides, alkyl halides or thiols, which are either free in solution or are coupled to proteins, polypeptides or labels.

Other embodiments are within the following claims.

I claim:

1. A compound of the formula:

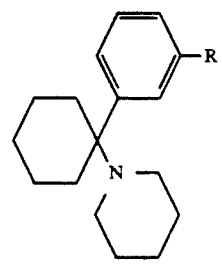

where R is a first linking group consisting of one of the following;

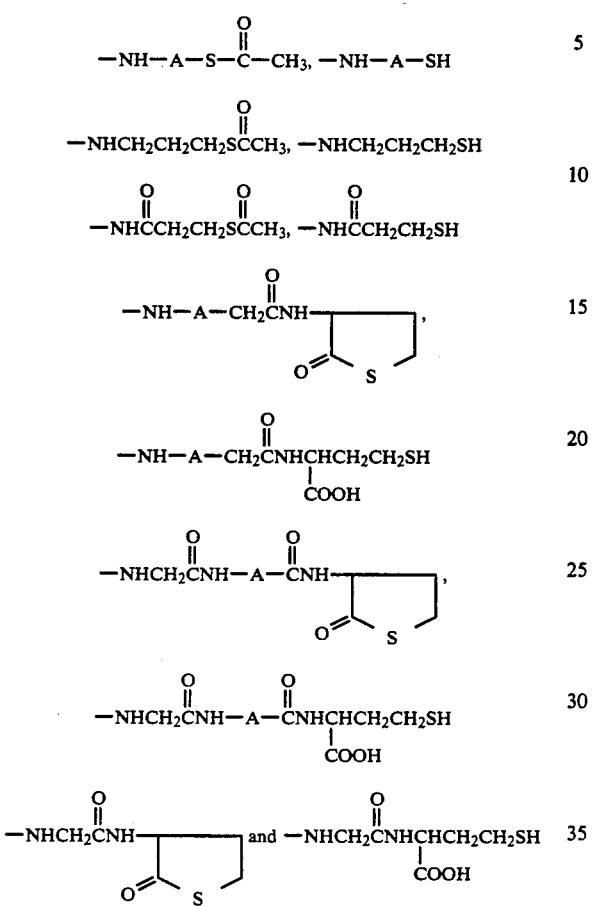

where A is a second hydrocarbyl linking group of from 1 to 20 carbons and from 0 to 10 heteroatoms selected from the group consisting of nitrogen, oxygen, and sulfur, which may either be in the chain or substituted on the chain which may be straight or branched.

2. An immunogenic protein or polypeptide molecule or a protein or polypeptide molecule or a label derivatized to a compound of the formula:

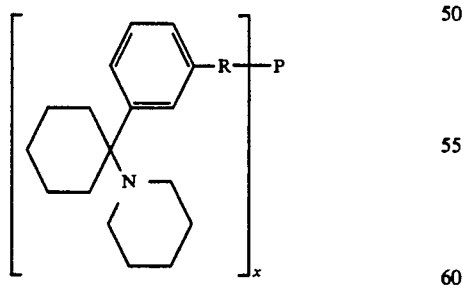

where P is an antigenic protein or polypeptide or a protein, polypeptide or label;
where X is at least one and not greater than 100;
where R is a first linking group consisting of one of the following:

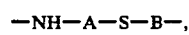

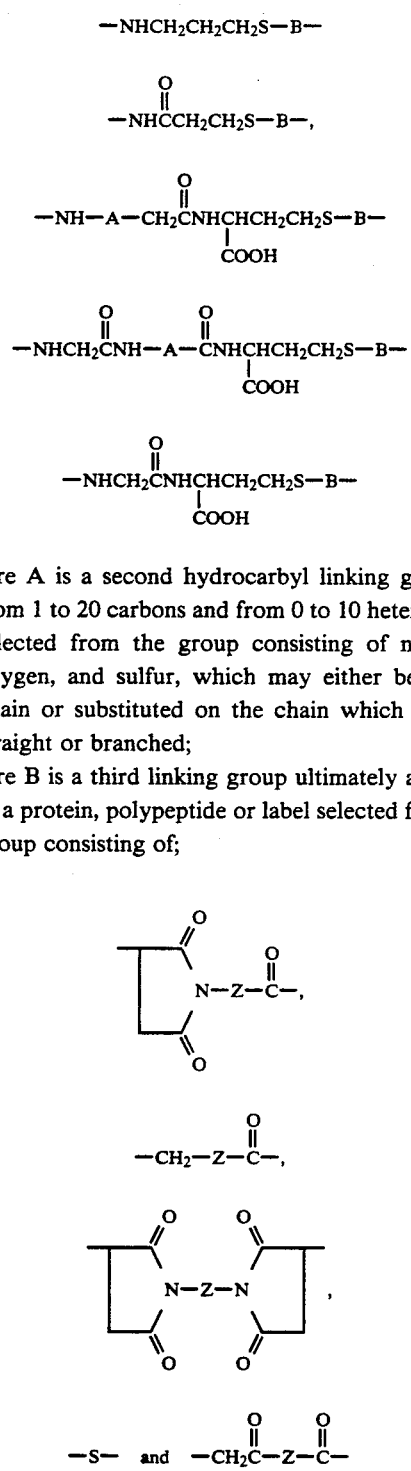

where A is a second hydrocarbyl linking group of from 1 to 20 carbons and from 0 to 10 heteroatoms selected from the group consisting of nitrogen, oxygen, and sulfur, which may either be in the chain or substituted on the chain which may be straight or branched;
where B is a third linking group ultimately attached to a protein, polypeptide or label selected from the group consisting of;

where Z is a fourth hydrocarbyl linking group of from 1 to 20 carbons and from 0 to 10 heteroatoms selected from the group consisting of nitrogen, oxygen, and sulfur, which may either be in the chain or substituted on the chain which may be straight or branched.

3. A compound of the formula:

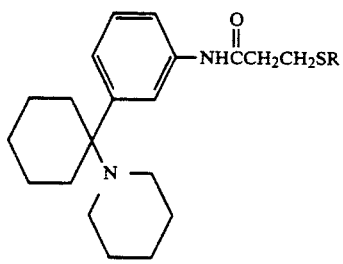

where R is H or CH₃.

4. An immunogenic protein or polypeptide molecule or a protein or polypeptide molecule or a label derivatized to a compound of the formula:

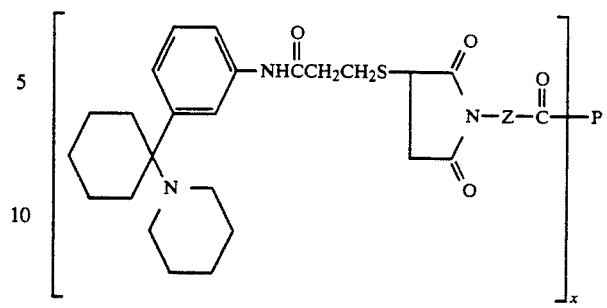

where P is an antigenic protein or polypeptide or a protein, polypeptide or label;

where X is at least one and not greater than 100;

where Z is a hydrocarbyl linking group of from 1 to 20 carbons and 0 to 10 heteroatoms selected from the group consisting of nitrogen, oxygen, and sulfur, which may either be in the chain or substituted on the chain which may be straight or branched.

* * * * *

UNITED STATES PATENT AND TRADEMARK OFFICE
CERTIFICATE OF CORRECTION

PATENT NO. : 5,331,109
DATED : JULY 19, 1994
INVENTOR(S) : KENNETH F. BUECHLER

It is certified that error appears in the above-indentified patent and that said Letters Patent is hereby corrected as shown below:

COLUMN 4, LINE 47: "Thioester" refers to [-S-O-] $-\underline{S-\overset{\overset{O}{\|}}{C}-}$.

COLUMN 7, LINE 63: where R is [-H]

COLUMN 13, LINE 17: where R is H or [$CH_3$]  $-\underline{\overset{\overset{O}{\|}}{C}CH_3}$.

Signed and Sealed this

Twenty-second Day of November, 1994

Attest:

BRUCE LEHMAN

*Attesting Officer*     *Commissioner of Patents and Trademarks*